United States Patent
Elomari et al.

(10) Patent No.: US 9,238,783 B2
(45) Date of Patent: *Jan. 19, 2016

(54) MONOESTER-BASED LUBRICANTS AND METHODS OF MAKING SAME

(71) Applicant: Chevron U.S.A. Inc., San Ramon, CA (US)

(72) Inventors: Saleh Ali Elomari, Fairfield, CA (US); Stephen Joseph Miller, San Francisco, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/682,542

(22) Filed: Nov. 20, 2012

(65) Prior Publication Data

US 2014/0142013 A1 May 22, 2014

(51) Int. Cl.
*C10M 129/95* (2006.01)
*C10M 129/70* (2006.01)
(Continued)

(52) U.S. Cl.
CPC .............. *C10M 105/34* (2013.01); *C07C 69/24* (2013.01); *C10M 2203/1006* (2013.01); *C10M 2203/1025* (2013.01); *C10M 2207/2815* (2013.01); *C10N 2220/021* (2013.01); *C10N 2220/022* (2013.01);
(Continued)

(58) Field of Classification Search
CPC ................... C10M 105/34; C10M 2203/1025; C10M 2203/1006; C10M 2207/2815; C07C 69/24; C10N 2220/022; C10N 2230/10; C10N 2220/021; C10N 2230/02

USPC ................................. 508/450–451, 459, 463
See application file for complete search history.

(56) References Cited

U.S. PATENT DOCUMENTS

| 2,510,300 A | 6/1950 | Walls |
| 2,797,196 A | 6/1957 | Dunn et al. |
| 2,936,856 A | 5/1960 | Braunwarth et al. |

(Continued)

FOREIGN PATENT DOCUMENTS

| CN | 103789070 A | 5/2014 |
| EP | 0374671 | 6/1990 |

(Continued)

OTHER PUBLICATIONS

Sheldon R.A., Kochi J.K., Metal-Catalyzed Oxidations of Organic Compounds, *Mechanistic Principles and Synthetic Methodology Including Biochemical Processes*, 1981, Academic Press, pp. 295-297 and pp. 162-171.

(Continued)

*Primary Examiner* — Pamela H Weiss
(74) *Attorney, Agent, or Firm* — Melissa M. Hayworth; Susan M. Abernathy

(57) ABSTRACT

The present invention is generally directed to monoester-based lubricant compositions. The present invention is also directed to methods of making these and other similar lubricant compositions. In some embodiments, the methods for making such monoester-based lubricants utilize a biomass precursor and/or low value Fischer-Tropsch (FT) olefins and/or alcohols so as to produce high value monoester-based lubricants. In some embodiments, such monoester-based lubricants are derived from FT olefins and fatty acids. The fatty acids can be from a bio-based source (i.e., biomass, renewable source) or can be derived from FT alcohols via oxidation.

11 Claims, 6 Drawing Sheets

(51) Int. Cl.
*C10M 105/34* (2006.01)
*C07C 69/24* (2006.01)

(52) U.S. Cl.
CPC ......... *C10N 2230/02* (2013.01); *C10N 2230/10* (2013.01)

(56) References Cited

U.S. PATENT DOCUMENTS

| | | | |
|---|---|---|---|
| 5,091,270 A * | 2/1992 | Ohya et al. | 428/843.4 |
| 5,232,910 A | 8/1993 | Mueller | |
| 5,252,554 A | 10/1993 | Mueller | |
| 5,318,954 A | 6/1994 | Mueller et al. | |
| 5,403,822 A | 4/1995 | Mueller et al. | |
| 5,441,927 A | 8/1995 | Mueller et al. | |
| 6,008,167 A | 12/1999 | Appelman et al. | |
| 6,100,223 A * | 8/2000 | Gee | 507/267 |
| 6,191,076 B1 * | 2/2001 | Gee | 507/267 |
| 6,281,404 B1 | 8/2001 | Miller | |
| 6,667,285 B1 * | 12/2003 | Kawahara et al. | 508/485 |
| 6,849,581 B1 | 2/2005 | Thompson et al. | |
| 7,008,909 B2 * | 3/2006 | Burgo et al. | 508/463 |
| 7,666,820 B2 | 2/2010 | Mueller et al. | |
| 8,148,305 B2 | 4/2012 | Westfechtel et al. | |
| 8,153,562 B2 | 4/2012 | Mueller et al. | |
| 8,236,735 B2 | 8/2012 | Maker et al. | |
| 9,115,303 B2 * | 8/2015 | Miller et al. | |
| 9,115,326 B2 * | 8/2015 | Elomari et al. | |
| 2003/0114316 A1 | 6/2003 | Patel | |
| 2005/0239662 A1 | 10/2005 | Patel | |
| 2006/0019840 A1 * | 1/2006 | Kawahara et al. | 508/280 |
| 2006/0073981 A1 | 4/2006 | Gee | |
| 2006/0254826 A1 | 11/2006 | Alberthy | |
| 2007/0219097 A1 | 9/2007 | Mueller | |
| 2010/0261627 A1 | 10/2010 | Miller et al. | |
| 2011/0009300 A1 | 1/2011 | Elomari et al. | |
| 2012/0053099 A1 | 3/2012 | Zhou et al. | |
| 2012/0329682 A1 | 12/2012 | Fefer | |
| 2013/0085090 A1 * | 4/2013 | Kim et al. | 508/404 |

FOREIGN PATENT DOCUMENTS

| | | |
|---|---|---|
| EP | 0374672 | 6/2009 |
| GB | 732376 A * | 6/1955 |
| WO | WO 9530818 A1 * | 11/1995 |
| WO | 9933932 | 7/1999 |
| WO | 9936387 | 7/1999 |
| WO | 2007137709 | 12/2007 |
| WO | 2008046554 | 4/2008 |
| WO | 2009053455 | 4/2009 |
| WO | 2009130445 A1 | 10/2009 |
| WO | 2009142922 | 11/2009 |

OTHER PUBLICATIONS

Schroder M., Osmium Tetraoxide Cis Hydroxylation of Unsaturated Substrates, Chem. Rev., 1980, 80, 1878-213.
Munch-Petersen J., 3-Methylheptanoic Acid, Organic Synthesis, Coll. vol. 5, p. 762 (1973); vol. 41, p. 60 (1961).
Spangler F.W., Allen C.F.H., y-Chloropropyl Acetate, Organic Synthesis, Coll. vol. 3, p. 203 (1955); vol. 29, p. 33 (1940).
Swern D., Findley T.W., and Scanian J.T., Epoxidation of Oleic Acid, Methyl Oleate and Oleyl Alcohol with Perbenzoic Acid, J. Am. Chem. Soc., 1944, 66 (11), 1925-1927.
International Search Report from corresponding application PCT/US2013/064117 mailed Feb. 5, 2014.

* cited by examiner

Internal (secondary) monoesters a representation of octylhexanoate monoesters a representation of decylhexanoate monoesters Characteristics of Esters of this Invention.

| Esters | Viscosity @100°C | Viscosity @40°C | Viscosity @0°C | Pour Point °C | BN Oxidator |
|---|---|---|---|---|---|
| Octyl Hexanoates | 0.9 cSt. | 2.2 cSt. | 5.8 cSt. | <-60 | 64 hrs |
| Decyl Hexanoates | 1.2 cSt. | 3.1 cSt. | 10.8 cSt. | <-60 | ----na------- |

FIG. 6A

Comparative oxidation data of lubricants

| Lubricant | BN Oxidator |
|---|---|
| Group I lubricants | 7.2 |
| Group III | 41.2 |
| Diesters tetradecyl-dilaureate | 26 |
| Diester hexadecyl-dilaureate | 38 |
| Cargill Agri-Pur 75 | 0.17* |
| Cargill Agri-Pur 82 | 0.3* |
| Cargill Agri-Pur 560 | 0.41* |

The Cargill products are commercial ester biolubricants.*

FIG. 6B

MONOESTER-BASED LUBRICANTS AND METHODS OF MAKING SAME

FIELD OF THE INVENTION

This invention relates to ester-based lubricants, and specifically to monoester-based lubricants, and methods of making them.

BACKGROUND OF THE INVENTION

Esters have been used as lubricating oils for over 50 years. They are used in a variety of applications ranging from jet engines to refrigeration, including drilling fluid. In fact, esters were the first synthetic crankcase motor oils in automotive applications. Esters, however, gave way to polyalphaolefins (PAOs) due to the lower cost of PAOs and their formulation similarities to mineral oils. In full synthetic motor oils, however, esters are almost always used in combination with PAOs to balance the effect on seals, additives solubility, volatility reduction, and energy efficiency improvement by enhanced lubricity.

Ester-based lubricants, in general, have excellent lubrication properties due to the polarity of the ester molecules of which they are comprised. The polar ester groups of such molecules strongly adhere to metal surfaces creating protective films which slow down the wear and tear of the metal surfaces. Such lubricants are less volatile than the traditional lubricants and tend to have much higher flash points and much lower vapor pressures. Ester lubricants are excellent solvents and dispersants, and can readily solvate and disperse the degradation by-products of oils. Therefore, they greatly reduce sludge buildup. While ester lubricants are stable to thermal and oxidative processes, the ester functionalities give microbes a means to do their biodegrading more efficiently and more effectively than their mineral oil-based analogues. However, the preparation of esters is more involved and can be more costly than the preparation of their PAO counterparts.

In view of the foregoing, a simpler, more efficient method of generating ester-based lubricants would be extremely useful—particularly wherein such methods utilize renewable raw materials in combination with converting low value Fischer-Tropsch (FT) olefins and alcohols to high value ester lubricants.

BRIEF DESCRIPTION OF THE INVENTION

The present invention is generally directed to monoester-based lubricant compositions. The present invention is also directed to methods of making these and other similar lubricant compositions. In some embodiments, the methods for making such monoester-based lubricants utilize a biomass precursor. In these or other embodiments, lubricant precursor species can also be sourced or derived from Fischer-Tropsch (FT) reaction products.

In some embodiments, the present invention is directed to lubricant compositions comprising a quantity of at least one monoester species, the monoester species having the structures depicted in FIG. 2 wherein $R_1$, $R_2$, and $R_3$, are the same or independently selected to form a monoester with a total carbon number ranging from 8 to 40.

In some or other embodiments, the present invention is directed to processes comprising the steps of (a) epoxidizing an internal olefin having a carbon number of from 6 to 22 to form an internal epoxide comprising an epoxide ring; (b) opening the epoxide ring by reduction of the epoxide to form an alcohol (secondary alcohol); and (c) esterifying the secondary alcohol with a $C_2$ to $C_{18}$ carboxylic acid to form a monoester species having viscosity and pour point suitable for use as a lubricant.

In some or other embodiments, the present invention is directed to processes (i.e., methods) comprising the steps of: (a) epoxidizing an internal olefin having a carbon number of from 6 to 22 to form an epoxide comprising an epoxide ring; (b) opening the epoxide ring via reduction methods to form an alcohol (secondary alcohol); and (c) esterifying the secondary alcohol with a $C_2$ to $C_{18}$ carboxylic acids or their acylating derivatives such as acyl chloride or anhydrides to form an internal (secondary) monoester species having viscosity and pour point suitable for use as a lubricant.

In some or still other embodiments, the present invention is directed to processes comprising the steps of: (a) epoxidizing a plurality of internal olefins, the olefins having a carbon number of from 6 to 22, to form a plurality of internal epoxides; (b) converting the epoxides to secondary alcohols; and (c) esterifying the alcohols with a $C_2$ to $C_{18}$ esterifying species to form a plurality of internal monoesters having viscosity and pour point suitable for use as a lubricant.

The olefins disclosed here may be alpha olefins produced by gas to liquid processes (GTL) refining processes, petrochemical processes, pyrolysis of waste plastics and other processes, are isomerized into internal olefins followed by conversion into monoesters. The alpha olefins are isomerized into internal olefins using double bond isomerization catalyst including silicoaluminophosphates molecular sieves such as SAPO-39 and medium pore aluminosilicates zeolites such as SSZ-32 and ZSM-23. The monoesters produced from the internal olefins possess superior oxidative and hydrolytic stability. Such monoesters also have low temperature properties that are desirable, such as lower cloud points and pour points. This results from inhibition in crystal formation.

The foregoing has outlined rather broadly the features of the present invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, and the advantages thereof, reference is now made to the following descriptions taken in conjunction with the accompanying drawings, in which:

FIG. 6(a) (Table 1) illustrates lubrication properties of monoester-based lubricants 1(a) and 1(b).

FIG. 6(b) (Table 2) compares Oxidation BN data for different lubricants.

DETAILED DESCRIPTION OF THE INVENTION

1. Introduction

Figure 1:
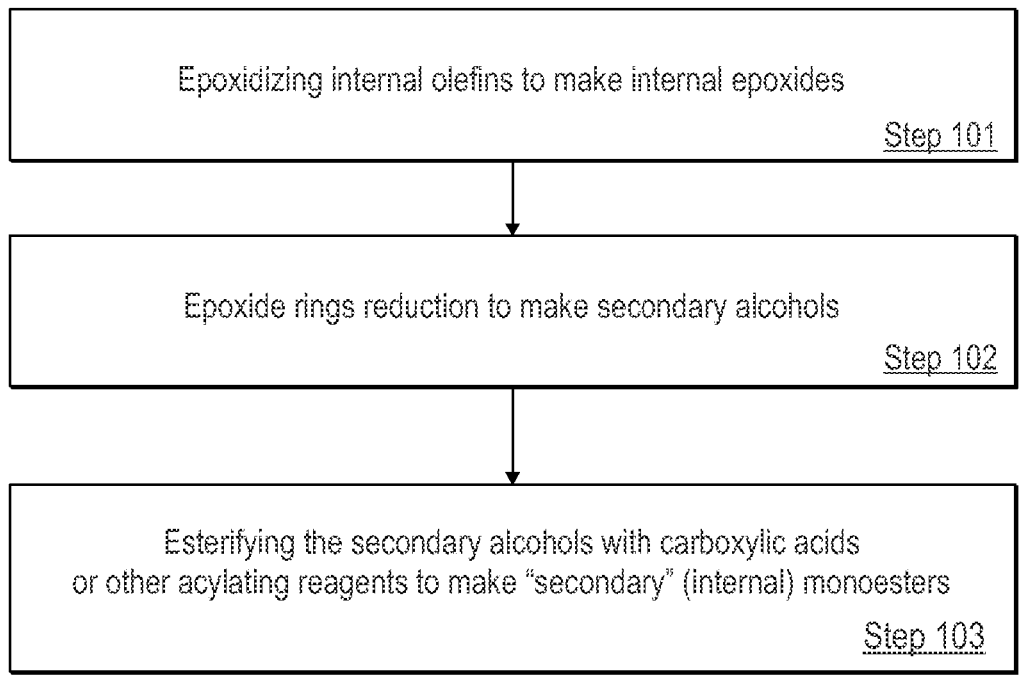
FIG. 1 is a flow diagram illustrating a method of making monoester based lubricant composition, in accordance with some embodiments of the present invention.

The present invention is directed to monoester-based lubricant compositions. The present invention is also directed to methods of making these and other similar lubricant compositions. In some embodiments, the methods for making such monoester-based lubricants utilize a biomass precursor and/or low value Fischer-Tropsch (FT) olefins and/or alcohols so as to produce high value monoester-based lubricants. In some embodiments, such monoester-based lubricants are derived from FT olefins and fatty (carboxylic) acids. In these or other embodiments, the fatty acids can be from a bio-based source (i.e., biomass, renewable source) or can be derived from FT alcohols via oxidation.

Because biolubricants and biofuels are increasingly gaining ground and becoming topics of focus for many in the oil industry, the use of biomass in the making of such above-mentioned lubricants could be attractive from several different perspectives. To the extent that biomass is so utilized in making the monoester-based lubricants of the present invention, such lubricants are deemed to be biolubricants.

2. Definitions

"Lubricants," as defined herein, are substances (usually a fluid under operating conditions) introduced between two moving surfaces so to reduce the friction and wear between them. Base oils used as motor oils are generally classified by the American Petroleum Institute as being mineral oils (Group I, II, and III) or synthetic oils (Group IV and V). See American Petroleum Institute (API) Publication Number 1509.

"Pour point," as defined herein, represents the lowest temperature at which a fluid will pour or flow. See, e.g., ASTM International Standard Test Methods D 5950-96, D 6892-03, and D 97.

"Cloud point," as defined herein, represents the temperature at which a fluid begins to phase separate due to crystal formation. See, e.g., ASTM Standard Test Methods D 5773-95, D 2500, D 5551, and D 5771.

"Centistoke," abbreviated "cSt," is a unit for kinematic viscosity of a fluid (e.g., a lubricant), wherein 1 centistoke equals 1 millimeter squared per second (1 cSt=1 mm$^2$/s). See, e.g., ASTM Standard Guide and Test Methods D 2270-04, D 445-06, D 6074, and D 2983.

With respect to describing molecules and/or molecular fragments herein, "$R_n$," where "n" is an index, refers to a hydrocarbon group, wherein the molecules and/or molecular fragments can be linear and/or branched.

As defined herein, "$C_n$," where "n" is an integer, describes a hydrocarbon molecule or fragment (e.g., an alkyl group) wherein "n" denotes the number of carbon atoms in the fragment or molecule.

The prefix "bio," as used herein, refers to an association with a renewable resource of biological origin, such as resource generally being exclusive of fossil fuels.

The term "internal olefin," as used herein, refers to an olefin (i.e., an alkene) having a non-terminal carbon-carbon double bond (C=C). This is in contrast to "α-olefins" which do bear a terminal carbon-carbon double bond.

3. Monoester Lubricant Compositions

Figure 2A:
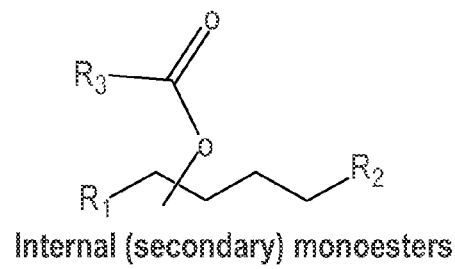
FIG. 2(a) is a diagram of a generic monoester.
Figure 2B:
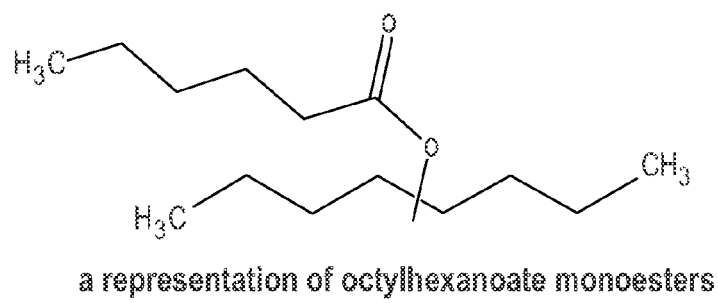
FIG. 2(b) illustrates a octyl hexanoate.
Figure 2C:
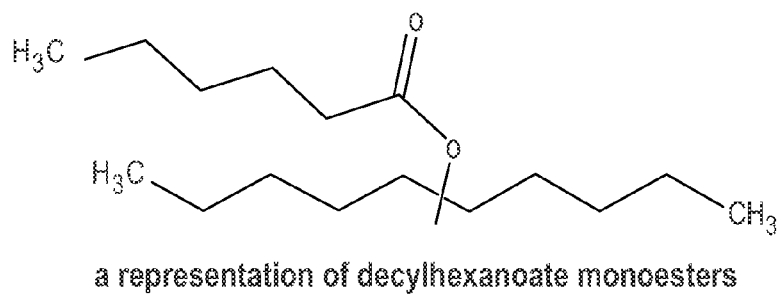
FIG. 2(c) illustrates a decyl hexanoate, two exemplary monoester-based compounds suitable for use as lubricants in accordance with some embodiments of the present invention.

In some embodiments, the present invention is generally directed to monoester-based lubricant compositions comprising a quantity of monoester species having a chemical structure as depicted in FIG. 2, where $R_1$, $R_2$, and $R_3$ are the same or independently selected so the total carbon number of the parent olefin would range from $C_6$ to $C_{22}$ and $R_3$ is selected so the total carbon number of the carboxylic acid ranges from $C_2$ to $C_{18}$. The total carbon number ranges from $C_8$ to $C_{40}$.

Regarding the above-mentioned monoester species, selection of $R_1$, $R_2$, and $R_3$ can follow any or all of several criteria. For example, in some embodiments, $R_1$, $R_2$, and $R_3$ are selected such that the kinematic viscosity of the composition of the monoesters at a temperature of 100° C. is typically in the range from 0.5 centistokes to 2.0 centistokes. In some or other embodiments, $R_1$, $R_2$, and $R_3$ are selected such that the pour point of the resulting lubricant is −20° C. or lower. In some embodiments, $R_1$ and $R_2$ are selected to have a combined carbon number (i.e., total number of carbon atoms) of from 6 to 22. The preferred range is $C_6$ to $C_{14}$, and the most preferred range is from $C_8$ to $C_{12}$. In these or other embodiments, $R_3$ is selected to have a combined carbon number of from 2 to 18. The preferred range is $C_6$ to $C_{14}$ and the most preferred range is $C_6$ to $C_{10}$. Depending on the embodiment, such resulting monoester species can have a molecular mass between 144 atomic mass units (a.m.u.) and 592 a.m.u.

In some embodiments, such above-described compositions are substantially homogeneous in terms of their monoester component. In some or other embodiments, the monoester component of such compositions comprises a variety (i.e., a mixture) of monoester species.

In some embodiments, the monoester-based lubricant composition comprises at least one monoester species derived from a $C_6$ to $C_{22}$ olefin and a $C_2$ to $C_{18}$ carboxylic acid. Typically, the monoester species are made by reacting the —OH groups (of secondary alcohols) with a different acid, but such monoester species can also be made by esterification of the secondary alcohols with the same acid.

In some of the above described embodiments, the olefins used in making the precursor secondary alcohols can be one of these olefins: hexenes, heptanes, octenes, nonenes, decenes, undecenes, dodecenes, tridecenes, tetradecenes, pentadecenes, hexadecenes, hepta decenes, octadecenes, nona-decenes, icosenes, henicosenes and docosenes or mixtures thereof.

In some of the above described embodiments, the carboxylic acids used of selected from the group consisting of: propionic acid, butyric acid, petanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, octadecanoic acid or mixtures thereof.

In some of the above-described embodiments, the monoester-based lubricant composition comprises a monoester species selected from the group consisting of hexanyl propanoate and isomers, hexanyl butyrate and isomers, hexanyl hexanoate and isomers, hexanyl octanoate and isomers, hexanyl decanoate and isomers, hexanyl laureate and isomers, hexanyl palmitate and isomers, hexanyl hexadecanoate and isomers, hexanyl stearate and isomers, octanyl propanoate and isomers, octanyl butyrate and isomers, octanyl hexanoate and isomers, octanyl octanoate and isomers, octanyl decanoate and isomers, octanyl laureate and isomers, octanyl palmitate and isomers, octanyl hexadecanoate and isomers, octanyl stearate and isomers, decanyl propanoate and isomers, decanyl butyrate and isomers, decanyl hexanoate and isomers, decanyl octanoate and isomers, decanyl decanoate and isomers, decanyl laureate and isomers, decanyl palmitate and isomers, decanyl hexadecanoate and isomers, decanyl stearate and isomers, dodecanyl propanoate and isomers, dodecanyl butyrate and isomers, dodecanyl hexanoate and isomers, dodecanyl octanoate and isomers, dodecanyl decanoate and isomers, dodecanyl laureate and isomers, dodecanyl palmitate and isomers, dodecanyl hexadecanoate and isomers, dodecanyl stearate and isomers, tetradecanyl propanoate and isomers, tetradecanyl butyrate and isomers, tetradecanyl hexanoate and isomers, tetradecanyl octanoate and isomers, tetradecanyl decanoate and isomers, tetradecanyl laureate and isomers, tetradecanyl palmitate and isomers, tetradecanyl hexadecanoate and isomers, tetradecanyl stearate and isomers, hexadecanyl propanoate and isomers, hexadecanyl butyrate and isomers, hexadecanyl hexanoate and isomers, hexadecanyl octanoate and isomers, hexadecanyl decanoate and isomers, hexadecanyl laureate and isomers, hexadecanyl palmitate and isomers, hexadecanyl hexadecanoate and isomers, hexadecanyl stearate and isomers, octadecanyl propanoate and isomers, octadecanyl butyrate and isomers, octadecanyl hexanoate and isomers, octadecanyl octanoate and isomers, octadecanyl decanoate and isomers, octadecanyl laureate and isomers, octadecanyl palmitate and isomers, octadecanyl hexadecanoate and isomers, octadecanyl stearate and isomers, icosanyl propanoate and isomers, icosanyl butyrate and isomers, icosanyl hexanoate and isomers, icosanyl octanoate and isomers, icosanyl decanoate and isomers, icosanyl laureate and isomers, icosanyl palmitate and isomers, icosanyl hexadecanoate and isomers, icosanyl stearate and isomers, docosanyl propanoate and isomers, docosanyl butyrate and isomers, docosanyl hexanoate and isomers, docosanyl octanoate and isomers, docosanyl decanoate and isomers, docosanyl laureate and isomers, docosanyl palmitate and isomers, docosanyl hexadecanoate and isomers, docosanyl stearate and mixtures thereof.

In some embodiments, the monoester-based lubricant composition further comprises a base oil selected from the group consisting of Group I oils, Group II oils, Group III oils, and mixtures thereof.

It is worth noting that in most applications, the above-described esters and their compositions are unlikely to be used as lubricants by themselves, but are usually used as blending stocks. As such, esters with higher pour points may also be used as blending stocks with other lubricant oils since they are very soluble in hydrocarbons and hydrocarbon-based oils.

4. Methods of Making Monoester Lubricants

As mentioned above, the present invention is additionally directed to methods of making the above-described lubricant compositions.

Referring to the flow diagram shown in FIG. 1, in some embodiments, processes for making the above-mentioned monoester species, typically having lubricating base oil viscosity and pour point, comprise the following steps: (Step 101) epoxidizing an internal olefin (or quantity of olefins) having a carbon number of from 6 to 22 to form an epoxide or a mixture of epoxides; (Step 102) opening the epoxide rings via reduction methods to form the corresponding mono secondary alcohol; and (Step 103) esterifying (i.e., subjecting to esterification) the secondary alcohol with a $C_3$ to $C_{18}$ carboxylic acid to form internal monoester species. Generally, lubricant compositions comprising such monoester species have a viscosity in the range from 0.5 centistokes to 2 centistokes at a temperature of 100° C.

In some embodiments, where a quantity of such monoester species is formed, the quantity of monoester species can be substantially homogeneous, or it can be a mixture of two or more different such monoester species.

In some such above-described method embodiments, the olefin used is a reaction product of a Fischer-Tropsch process. In these or other embodiments, the carboxylic acid can be derived from alcohols generated by a Fischer-Tropsch process and/or it can be a bio-derived fatty acid.

In some embodiments, the olefin is an α-olefin (i.e., an olefin having a double bond at a chain terminus). In such embodiments, it is usually necessary to isomerize the olefin so as to internalize the double bond. Such isomerization is typically carried out catalytically using a catalyst such as, but not limited to, crystalline aluminosilicate and like materials and aluminophosphates. See, e.g., U.S. Pat. Nos. 2,537,283; 3,211,801; 3,270,085; 3,327,014; 3,304,343; 3,448,164; 4,593,146; 3,723,564 and 6,281,404; the last of which claims a crystalline aluminophosphate-based catalyst with 1-dimensional pores of size between 3.8 Å and 5 Å.

Figure 3:
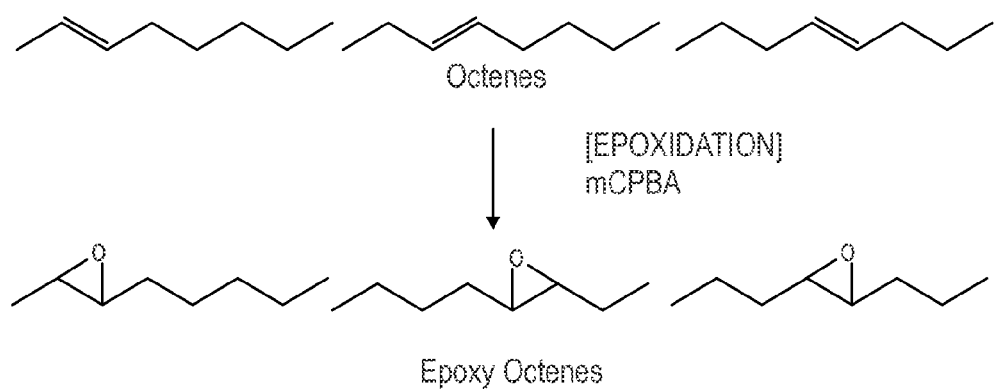
FIG. 3 (Scheme 1) is a chemical flow diagram illustrating the epoxidation step of Example 1 in monoester preparation.

As an example of such above-described isomerizing and as indicated in Scheme 1 (FIG. 3), Fischer-Tropsch alpha olefins (α-olefins) can be isomerized to the corresponding internal olefins followed by epoxidation. The epoxides can then be transformed to the corresponding secondary mono alcohols via epoxide ring reduction followed by esterifying (i.e., di-esterification) with the appropriate carboxylic acids or their acylating derivatives. It is typically necessary to convert alpha olefins to internal olefins because monoesters of alpha olefins, especially short chain alpha olefins, tend to be solids or waxes. "Internalizing" alpha olefins followed by transformation to the monoester functionalities introduces branching along the chain in the produced esters and thus reduces the symmetry of the molecules which in turn reduces the pour point of the intended products. Internalizing the ester may also enhance the oxidative and hydrolytic stability. Internal esters show surprising hydrolytic and oxidative stabilities that are much superior to those of terminal esters. Internalizing the ester makes it sterically more hindered and that may contribute to the oxidative and hydrolytic stabilities.

The ester groups with their polar character would further enhance the viscosity of the final product. Branching, introduced by internalizing the ester groups, will enhance the cold temperature properties such as pour and cloud points. Viscosity can be increased by increasing the carbon number of the internal olefin or the acid used in the esterification.

Regarding the step of epoxidizing (i.e., the epoxidation step), in some embodiments, the above-described olefin (preferably an internal olefin) can be reacted with a peroxide (e.g., $H_2O_2$) or a peroxy acid (e.g., peroxyacetic acid) to generate an epoxide. See, e.g., D. Swern, in *Organic Peroxides Vol. II*, Wiley-Interscience, New York, 1971, pp. 355-533; and B. Plesnicar, in Oxidation in *Organic Chemistry, Part C*, W. Trahanovsky (ed.), Academic Press, New York 1978, pp. 221-253. Olefins can be efficiently transformed to the corresponding diols by highly selective reagent such as osmium tetra-oxide (M. Schroder, Chem. Rev. vol. 80, p. 187, 1980) and potassium permanganate (Sheldon and Kochi, in Metal-Catalyzed Oxidation of Organic Compounds, pp. 162-171 and 294-296, Academic Press, New York, 1981).

Regarding the step of epoxide ring opening to the corresponding secondary mono alcohols, this step is done by epoxide ring reduction using metal hydrides reduction procedures or noble metal-catalyzed hydrogenations processes. Both procedures are very effective at making the needed secondary alcohols for internal epoxides.

Regarding the step of esterifying (esterification), an acid is typically used to catalyze the esterification reaction of alcohols and carboxylic acids. Suitable acids for esterification include, but are not limited to, sulfuric acid (Munch-Peterson, Org. Synth., V, p. 762, 1973), sulfonic acid (Allen and Sprangler, Org. Synth., III, p. 203, 1955), hydrochloric acid (Eliel et al., Org Synth., IV, p. 169, 1963), and phosphoric acid (among others). In some embodiments, the carboxylic acid used in this step is first converted to an acyl chloride (via, e.g., thionyl chloride or PCl3). Alternatively, an acyl chloride could be employed directly. Wherein an acyl chloride is used, an acid catalyst is not needed and a base such as pyridine, 4-dimethylaminopyridine (DMAP) or triethylamine (TEA) is typically added to react with an HCl produced. When pyridine or DMAP is used, it is believed that these amines also act as a catalyst by forming a more reactive acylating intermediate. See, e.g., Fersh et al., J. Am. Chem. Soc., vol. 92, pp. 5432-5442, 1970; and Hofle et al., Angew. Chem. Int. Ed. Engl., vol. 17, p. 569, 1978.

Regardless of the source of the olefin, in some embodiments, the carboxylic acid used in the above-described method is derived from biomass. In some such embodiments, this involves the extraction of some oil (e.g., triglyceride) component from the biomass and hydrolysis of the triglycerides of which the oil component is comprised so as to form free carboxylic acids.

Using a synthetic strategy in accordance with that outlined in Scheme 1 (FIG. 3), Scheme 2 (FIG. 4), and Scheme 3 (FIG. 5), a mixture of internal octenes was converted to the corresponding mixture of internal monoester derivatives, octyl hexanoates and octyl decanoates via acylation of the octyl alcohols intermediates with hexanoyl and decanoyl chlorides, respectively. The Examples below explain this process in more detail. Octyl and decyl hexanoates are particularly suitable for use in drilling fluid compositions.

5. Variations

Variations (i.e., alternate embodiments) on the above-described lubricant compositions include, but are not limited to, utilizing mixtures of isomeric olefins and or mixtures of olefins having a different number of carbons. This leads to monoester mixtures in the product compositions.

Variations on the above-described processes include, but are not limited to, using carboxylic acids derived from FT alcohols by oxidation.

6. Examples

The following examples are provided to demonstrate particular embodiments of the present invention. It should be appreciated by those of skill in the art that the methods disclosed in the examples which follow merely represent exemplary embodiments of the present invention. However, those of skill in the art should, in light of the present disclosure, appreciate that many changes can be made in the specific embodiments described and still obtain a like or similar result without departing from the spirit and scope of the present invention.

As an exemplary synthetic procedure, the synthesis of a monoester, octyl hexanoate is described in Examples 1-3. This procedure is representative for making monoesters from internal olefins and carboxylic acid chlorides (acyl chlorides), in accordance with some embodiments of the present invention.

EXAMPLE 1

This Example serves to illustrate synthesis of a secondary alcohol en route to synthesis of a monoester species, in accordance with some embodiments of the present invention.

Epoxidation of Octenes into Epoxy Octanes

A mixture of 2-octene, 3-octene and 4-octene (1:1:1 mixture), purchased from Aldrich Chemical company, were epoxidized as follows using the general procedure described below (Scheme 1). To a stirred solution of 509 grams (2.95 mol) of 77% mCPBA (meta-chloroperoxybenzoic acid) in 2000 mL n-hexane in an ice bath, 265 grams (2.36 mol) of 2-octene, 3-octene and 4-octene (1:1:1) mixture were added drop-wise via an addition funnel over a period of 60 minutes. The resulting reaction mixture was stirred over 0° C. for 2 hrs. Then, the ice bath was removed and the reaction was allowed to stir overnight. The resulting milky solution was subsequently filtered to remove meta-chloro-benzoic acid that formed therein. The filtrate was then washed with a 10% aqueous solution of sodium bicarbonate. The organic layer was dried over anhydrous magnesium sulfate while stirring for 1 hr. The organic solvent (n-hexane) was removed by distillation at atmospheric pressure and 67-71° C. IR and NMR analysis and GCMS spectroscopy on the remaining solution confirmed the presence of the epoxide mixture with little residual n-hexane. This solution was used as is for next step (reduction of the epoxides to the corresponding secondary alcohols) without any further attempt to remove the remaining hexane. The epoxide is somewhat volatile. Care must be taken to prevent any appreciable loss by distillation or condensation on a rotary evaporator.

Epoxidation was also accomplished using formic acid/hydrogen epoxide solution of 1:1.5 parts.

EXAMPLE 2

Reduction of 2,3-Epoxy Octanes to Secondary Octanols

Synthesis Examples

The epoxy octanes with little residual hexane produced according to example 1 were reduced with lithium aluminum hydride in THF (Tetrahydrofuran) according to the procedure described below. The products from example 1 were divided into two equal portions and each portion was reduced separately with lithium aluminum hydride in anhydrous THF. Assuming full conversion of the octenes to epoxides in Example 1, each portion was assumed to contain 1.18 moles (151.3 grams) of epoxy octanes. Accordingly, a suspension of 56 grams (1.48 mol.) of lithium aluminum hydride in 1000 mL anhydrous THF in 3-liter 3-neck reaction flask equipped with an overhead stirrer and reflux condenser, was cooled down to 0° C. in an ice-bath. To this suspension and while stirring, one of the two portions of the epoxy octanes mixture (presuming 151.3 grams; 1.18 mol.) was added drop-wise via a sealed dropping funnel. Once the addition was complete, an additional 100 ml of THF was added via the dropping funnel. The reaction mixture was left to stir at 0° C. for 2 hrs. The ice-bath was then removed and the reaction left to stir overnight. The reaction was then heated to reflux for an hour or so to ensure reduction completion. The reaction progress was monitored by NMR and IR analysis on small aliquots work-up. Once completed, the heat source was replaced with an ice-bath and the reaction was worked up by first diluting with 500 ml THF and then adding 550 ml of 15% NaOH solution via a dropping funnel with vigorous stirring and not allowing the temperature of the reaction to rise above room temperature (very slow addition). The addition continued until all the grey solution transformed into a milky solution which was left to stir for addition 30 minutes. The stirring was stopped and the solution nicely separated into a clear liquid phase and a fine white precipitate. The mixture was filtered and the filtrate was dried over anhydrous MgSO$_4$ and then concentrated on a rotary evaporator to remove the solvent THF and afford a mixture of 2-octanol, 3-octanol, and 4-octanol as colorless viscous oil that turned into a very soft waxy substance while standing at room temperature for few days. The reduction afforded 132 grams of the alcohols or 86% yield for the two reactions described in examples 1 and 2. Reduction of the second portion of the epoxy octanes gave similar results with 84% overall yield.

Figure 4:
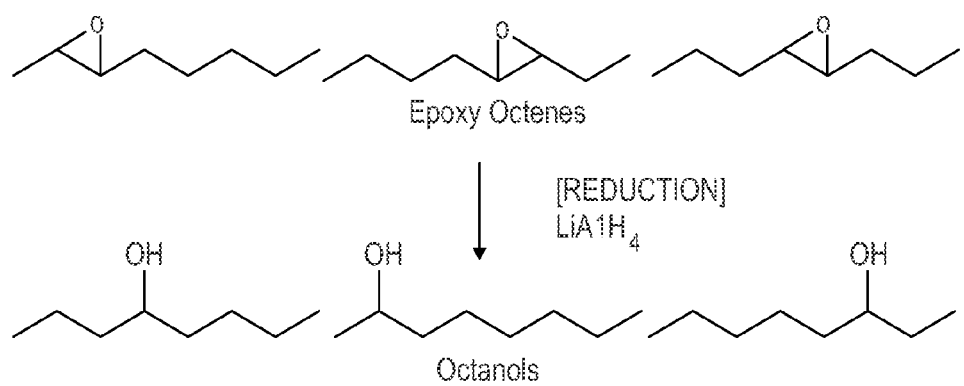
FIG. 4 (Scheme 2) is a chemical flow diagram illustrating, in monoester preparation, the epoxide ring opening step (reduction) to create an alcohol of Example 2.
Figure 5:
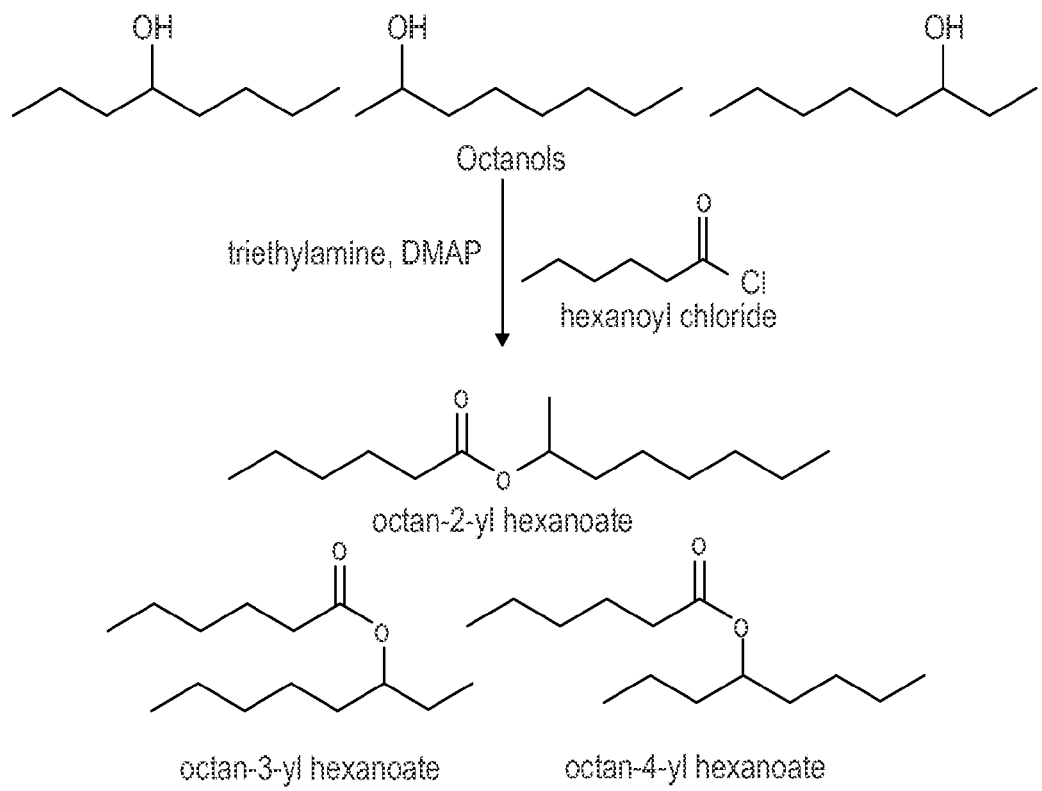
FIG. 5 (Scheme 3) illustrates esterification of octanols with hexanoyl chloride for the synthesis of octyl hexanoates.

Reduction was also accomplished by mild hydrogenation over Pd/C catalyst on small scale, as depicted in Scheme 2 (see FIG. 4).

Aside from metal hydrides reductions, the epoxides were also reduced with quantitative yields by mild hydrogenation processes using Pt-based and Pd-based hydrogenation catalysts at 100-150 PSI hydrogen pressure and temperature of 35-50 C.

EXAMPLE 3

Esterification of Octanols with Hexanoyl Chloride: Synthesis of Octyl Hexanoates The mixture of 2-octanol, 3-octanol, and 4-octanol prepared in example 2 was esterified according to the procedure below using hexanoyl chloride as the esterification agent as shown in Scheme 3. To a solution of 130.5 grams (1 mol.) of the octanols mixture in 1000 ml cyclohexane in a 3-neck 3 L round bottom reaction vessel equipped with an overhead stirrer and reflux condenser, 126.5 grams (1.25 mol.) of triethylamine and 6.5 grams (0.05 mol.) of 4-N,N-dimethylaminopyridine (DMAP). The mixture was cooled down by means of an ice-bath and left to stir at around 0° C. for 15 minutes. To the stirring cold solution, 148 grams (1.1 mol.) of hexanoyl chloride was added drop-wise via a dropping funnel over 45 minutes. Once all hexanoyl chloride was added, the reaction was left to stir and warm slowly to room temperature. The reaction, then, was refluxed and monitored by NMR and IR analysis. Once the reaction was completed, the resulting milky creamy solution was worked up by adding water until all the solids disappeared and a clear solution formed (two phase solution). The two phase solution was separated in a separatory funnel and the organic phase was washed with water and brine and saved. The aqueous phase was extracted with ethyl acetate. The ethyl acetate extract was washed with brine and was combined to the organic phase. The organic phase, containing the esters, was dried over anhydrous $MgSO_4$, filtered and concentrated on a rotary evaporator to give 218 grams (96% yields) of the esters mixture as slightly orange-colored oil. The product was passed through 15 cm×5 cm silica gel plug and flushed with hexane. The hexane was removed on a rotary evaporator to give the product as colorless oil (214 gm were recovered).

Using identical synthesis procedures, decyl hexanoates were synthesized in similar yields.

EXAMPLE 4

Esterification with Hexanoic Acid Using $H_3PO_4$ as Catalyst

The mixture of octanols was also esterified with hexanoic acid in toluene and using phosphoric acid as catalyst according to the procedure shown below. The reaction apparatus consisted of a 3-neck 1 L reaction flask equipped with an overhead stirrer, reflux condenser with a Dean-Stark trap and a heating mantle. The reaction vessel was charged with 50 gm (0.38 mol.) of octanols mixture, 66 gm (0.57 mol.) hexanoic acid, 5 gm of 85% phosphoric acid, and 250 ml toluene. The mixture was heated at reflux (~110° C.) for 6 hrs and left to stir at reflux overnight. One more gram of 85% H3PO4 was added and the reaction was left to continue stirring at reflux until no more water formation was observed (as indicated by the level of water collected in the Dean-Stark trap). In all, the reaction stirred for approximately 36 hrs. The reaction was then cooled down and worked up by removing the toluene on a rotary evaporator followed by extraction in diethyl ether and extensive washing with warm water (4×500 ml) followed by rinsing with 300 ml of saturated sodium bicarbonate solution to remove any residual acids (organic and inorganic) and with brine solution (300 ml). The ether extract was dried over anhydrous $MgSO_4$, filtered and concentrated on a rotary evaporated to remove ether. The reaction afforded 76 gram of faint yellow oil. The oil was then passed through a 10 cm×4 cm silica gel plug to remove any residual acids. After the final purification step, 73 grams of the desired esters (octyl hexanoates) was recovered as colorless oil with a sweet odor.

EXAMPLE 5

The procedure described in example 4 was repeated but at a 2 liter scale and 2 gallons of the octyl hexanoates were produced using this scale in few syntheses.

EXAMPLE 6

Lubrication Properties of Octyl Hexanoates

FIG. 6 (Tablet) shows the lubrication properties of octyl hexanoates and decyl hexanoates. Both of these esters are particularly suitable for use in drilling fluids.

EXAMPLE 7

Oxidator BN Test

The octyl hexanoate mixture was evaluated for oxidation stability by measuring how much time it takes for a given amount of the ester to absorb 1 liter of Oxygen using the Oxidator BN test. Octyl hexanoates exhibited superior oxidation stability with 64 hrs (see Tables 1 and 2, FIGS. 6(a) and 6(b). Table 2 provides comparative Oxidator BN information for other lubricants.

7 Summary

In summary, the present invention provides for monoester-based lubricant compositions. The present invention also provides for methods (processes) of making these and other similar lubricant compositions. In some embodiments, the methods for making such monoester-based lubricants utilize a biomass precursor and/or low value Fischer-Tropsch olefins and/or alcohols so as to produce high value monoester-based lubricants. In some embodiments, such monoester-based lubricants are derived from FT olefins and fatty acids. The fatty acids can be from a bio-based source (i.e., biomass, renewable source) or can be derived from FT alcohols via oxidation.

All patents and publications referenced herein are hereby incorporated by reference to the extent not inconsistent herewith. It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise than as specifically described without actually departing from the spirit and scope of the present invention as defined by the appended claims.

What is claimed is:

1. A lubricant composition comprising:
an isomeric mixture of at least one monoester species, the monoester species being a secondary monoester and having the following structure:

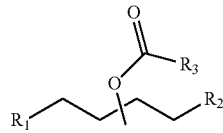

having a total carbon number ranging from $C_8$ to $C_{40}$, wherein $R_1$, $R_2$, and $R_3$ are independently selected from alkyl groups; and
a base oil selected from the group consisting of Group I oils, Group II oils, Group III oils, and mixtures thereof.

2. The lubricant composition of claim 1, wherein the kinematic viscosity of the composition at a temperature of 100° C. is in the range from 0.5 centistokes through 2 centistokes.

3. The lubricant composition of claim 1, wherein the pour point is −20° C. or lower.

4. The lubricant composition of claim 1, wherein $R_1$ and $R_2$ are selected to have a combined carbon number of from 6 to 22.

5. The lubricant composition of claim 1, wherein $R_3$ has a carbon number of from 2 to 18.

6. The lubricant composition of claim 1, wherein the secondary monoester species is decyl hexanoate and the isomeric mixture comprises isomers of octyl hexanoate.

7. The lubricant composition of claim 1, wherein the secondary monoester species is decyl hexanoate and the isomeric mixture comprises isomers of decyl hexanoate.

8. The lubricant composition of claim 1, wherein the lubricant compositon has a kinematic viscosity at a temperature of 100° C. of 0.5 cSt to 2 cSt and a pour point of −20° C. or lower.

9. A lubricant composition comprising an isomeric mixture of at least one monoester species, the monoester species being a secondary monoester selected from the group consisting of octyl hexanoate, decyl hexanoate, and mixtures thereof.

10. The lubricant composition of claim 9, wherein the secondary monoester species is octyl hexaonate and has an Oxidator BN value of 64 hours.

11. The lubricant composition of claim 9, wherein the lubricant composition has a kinematic viscosity at a temperature of 100° C. of 0.5 cSt to 2 cSt and a pour point of −20° C. or lower.

* * * * *

UNITED STATES PATENT AND TRADEMARK OFFICE
CERTIFICATE OF CORRECTION

PATENT NO. : 9,238,783 B2  
APPLICATION NO. : 13/682542  
DATED : January 19, 2016  
INVENTOR(S) : Saleh Ali Elomari et al.

It is certified that error appears in the above-identified patent and that said Letters Patent is hereby corrected as shown below:

Claims
In Claim 6, column 12, line 7:
"secondary monoester species is decyl hexanoate and the isomeric mixture comprises isomers of octyl hexanoate" should read --secondary monoester species is octyl hexanoate and the isomeric mixture comprises isomers of octyl hexanoate--.

Signed and Sealed this
Twelfth Day of April, 2016

Michelle K. Lee
*Director of the United States Patent and Trademark Office*